(12) United States Patent
Henke et al.

(10) Patent No.: US 12,721,984 B2
(45) Date of Patent: Sep. 1, 2026

(54) APPARATUS FOR PRODUCING MICRO-ARRAYS, AND METHOD FOR PRODUCING A MICRO-ARRAY

(71) Applicant: LTS Lohmann Therapie-Systeme AG, Andernach (DE)

(72) Inventors: Stefan Henke, Kirchen (DE); Jörg Bender, Cologne (DE); Hagen Trommer, Leipzig (DE); Sebastian Scherr, Neuhäusel (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 836 days.

(21) Appl. No.: 17/917,318

(22) PCT Filed: Mar. 25, 2021

(86) PCT No.: PCT/EP2021/057804
§ 371 (c)(1),
(2) Date: Oct. 6, 2022

(87) PCT Pub. No.: WO2021/204557
PCT Pub. Date: Oct. 14, 2021

(65) Prior Publication Data

US 2023/0149680 A1 May 18, 2023

(30) Foreign Application Priority Data

Apr. 9, 2020 (DE) ..................... 10 2020 204 651.4

(51) Int. Cl.
*A61M 37/00* (2006.01)

(52) U.S. Cl.
CPC . *A61M 37/0015* (2013.01); *A61M 2037/0053* (2013.01)

(58) Field of Classification Search
CPC ...... A61M 37/0015; A61M 2037/0053; A61M 2037/0046; B29L 2031/756
See application file for complete search history.

(56) References Cited

U.S. PATENT DOCUMENTS

| | | | |
|---|---|---|---|
| 10,105,526 | B2 | 10/2018 | Scherr et al. |
| 11,648,382 | B2 | 5/2023 | Chang et al. |
| 2001/0044180 | A1 | 11/2001 | Schrems |
| 2005/0164464 | A1 | 7/2005 | Hecht et al. |
| 2008/0269685 | A1 | 10/2008 | Singh et al. |

(Continued)

FOREIGN PATENT DOCUMENTS

| | | | |
|---|---|---|---|
| JP | 2016164307 | A | 9/2016 |
| KR | 1020170135773 | A | 12/2017 |

(Continued)

*Primary Examiner* — JaMel M Nelson
*Assistant Examiner* — Erica Hartsell Funk
(74) *Attorney, Agent, or Firm* — The Webb Law Firm

(57) ABSTRACT

An apparatus for producing microarrays includes a die. A plurality of cavities is formed in the die. A cover element is additionally provided in order to cover regions between the cavities. In this manner it is possible to remove an active agent-containing liquid from the regions formed between the cavities when metering said liquid. This is achieved in that the cover element is removed again. An active agent-free liquid can then be metered, with which a remaining portion of the cavities are filled, and a support layer is formed on the upper surface of the die.

2 Claims, 1 Drawing Sheet

(56) References Cited

U.S. PATENT DOCUMENTS

| | | | | |
|---|---|---|---|---|
| 2011/0281102 | A1 | 11/2011 | Scholten et al. | |
| 2019/0046479 | A1* | 2/2019 | Pathak .............. | A61M 37/0076 |
| 2020/0324096 | A1* | 10/2020 | Hwang ................. | B29C 39/026 |

FOREIGN PATENT DOCUMENTS

| | | | | |
|---|---|---|---|---|
| WO | 2015117938 | A1 | 8/2015 | |
| WO | 2016033540 | A1 | 3/2016 | |
| WO | 2019045254 | A1 | 3/2019 | |
| WO | WO-2019103268 | A1 * | 5/2019 | ........... B29C 39/026 |

* cited by examiner 14
16
12
16
12
16
12
10

20
18
22
10

12
12
12
26
26
26
26
18
10

24
24
24
28
30
10

APPARATUS FOR PRODUCING MICRO-ARRAYS, AND METHOD FOR PRODUCING A MICRO-ARRAY

CROSS-REFERENCE TO RELATED APPLICATIONS

This application is the United States national phase of International Application No. PCT/EP2021/057804 filed Mar. 25, 2021, and claims priority to German Patent Application No. 10 2020 204 651.4 filed Apr. 9, 2020, the disclosures of which are hereby incorporated by reference in their entirety.

BACKGROUND OF THE DISCLOSURE

Field of the Disclosure

The disclosure relates to an apparatus for producing microarrays, and to a method for producing a microarray.

Description of Related Art

Microarrays comprise a plurality of microneedles which are typically arranged on a support element, such as a patch, a plaster or the like, or are connected to a support element. Microarrays of this kind comprise a high number of microneedles. In this case, the length of the needles is selected such that, when the microneedles penetrate into the skin of a patient, they penetrate into the skin only to such an extent that the needle tips penetrating as far as possible do not contact nerves or blood vessels. The microneedles comprise an active agent or a medicine. In this case, the corresponding active agent can be applied to a surface or outside of the needles. Likewise, the needle itself can comprise a corresponding active agent, wherein the needle material then dissolves in the patients skin. The application of the active agent takes place thereby.

The use of dies, for example made of silicone, is known for producing microarrays. Said dies comprise a plurality of cavities, which form the microneedles. A liquid or mass provided with the corresponding active agent is metered onto the die in such a way that the cavities are filled with the corresponding liquid, at least in part. In this case, it is possible to meter an amount of active agent-containing liquid onto the die that is so large that a support layer or a support element results on the upper surface of the die, which layer or element interconnects the individual needles. Since in this case the entire microarray is produced from an active agent-containing material and this material is expensive, it is furthermore known to produce microarrays from a plurality of layers. In this case, initially a first, active agent-containing, liquid is metered into the cavities of the die. Optionally, after a first drying step, a further active agent-free liquid is metered. It is optionally also possible for more than two layers to be provided. A disadvantage when producing a microarray from a plurality of layers is that, during metering of the active agent-containing liquid, this frequently reaches not only into the tips of the cavities, but rather is also arranged on the upper surface of the die and the upper edges or the upper inner walls of the cavities. The active agent located here is not delivered to the patients.

SUMMARY OF THE DISCLOSURE

The object of the disclosure is that of providing an apparatus for producing microarrays, by means of which it is ensured that active agent-containing liquid is arranged substantially only in the cavity tips. The object of the invention is furthermore that of providing a corresponding method for producing a microarray.

The object is achieved by an apparatus for producing microarrays, and by a method for producing a microarray as described herein.

The apparatus according to the disclosure for producing microarrays comprises a die having a plurality of cavities. Furthermore, a cover element is provided, which covers regions between the cavities. As a result it is possible, in particular in the case of a multi-layer microarray, to first place the cover element on the upper surface of the die, such that regions between the cavities are covered, at least in part. In the next step, the active agent-containing material, in particular the corresponding liquid, is metered. The portions of the liquid which do not enter the cavities, but are rather deposited on the cover element, can be removed from the die in a simple manner, by removing the cover element. The second active agent-free liquid can then be metered in the next step. The corresponding support layer or the corresponding support element can then be formed thereby. In this case, the first active agent-containing liquid is metered in at an amount such that the cavities are filled only in part. This results in needle tips comprising active agent. The upper part of the individual needles is then filled with an active agent-free material. In addition, a cap layer is applied to the upper surface of the die, which forms the support element.

The die preferably comprises an upper surface, on which the openings of the cavities are formed. The cavities are in particular formed in the shape of pyramids, and have a square cross-section. The cavities can also be designed as spheres having a round cross-section. The cover element is designed such that it rest on the upper surface of the die, in particular during metering of active agent-containing liquid. In this case, the cover element is designed according to a template or foil comprising openings, such that substantially only the regions between the cavities are covered by the cover element.

The cover element is preferably placed only on the upper surface of the die, and can thus be removed in a simple manner, in order to then meter in an active agent-free liquid in a subsequent step. Removing the cover element also removes active agent-containing liquid which is not arranged in the cavity tips.

In a preferred development of the disclosure, the cover element is a foil or a template. It is particularly preferable for the cover element to comprise projections which protrude into the cavities. In particular, the projections are designed such that they protrude into the cavities in an upper region, and rest on the inner walls of the cavities. It is thereby possible, upon removal of the cover element, to also remove active agent-containing liquid in the upper region of the cavities. In this case, the upper region of the cavities is the region which faces in the direction of the upper surface of the die.

In particular, at least individual projections are designed such that they are peripheral in the manner of a collar. At least individual projections thus protrude, as a peripheral collar, into one cavity in each case. Preferably all the projections are designed in this way. It is particularly preferred for at least individual projections to be designed such that, in the upper region of the corresponding cavity, they completely cover said region.

The apparatus according to the disclosure makes it possible to significantly improve the quality of microarrays since the active agent-containing liquid is substantially present only in the region of the tips of the microneedles.

The disclosure furthermore relates to a method for producing a microarray, wherein it is particularly preferred for this to be performed by means of the above-described apparatus according to the disclosure. In a first step of the method according to the disclosure, a cover element is arranged on a die, in particular on an upper surface of the die. In this case, the cover element is designed such that it covers regions located between the cavities of the die. The cover element can preferably be designed as described above, and in particular comprise projections which protrude into the cavities.

The metering of an active agent-containing liquid into the cavities takes place in the next step. In the process, liquid also reaches the cover element. The cover element is then removed in the next step. Optionally, a drying step can take place before the removal of the cover element, in which step the active agent-containing liquid cures, at least in part by evaporation of solvent.

Following the removal of the cover element, an active agent-free liquid is metered, both into the cavities and onto the upper surface of the die. As a result, a support layer or a support element of the microarray is formed.

In a particularly preferred embodiment, the individual steps take place in the sequence described above.

Optionally, one or more intermediate layers can also be metered, which layers serve to stabilize the microarray and/or contain another active agent.

BRIEF DESCRIPTION OF THE DRAWINGS

The disclosure will be explained in greater detail in the following on the basis of a preferred embodiment, with reference to the accompanying drawings, in which.

DETAILED DESCRIPTION

Figures 1, 2, 3, 4:
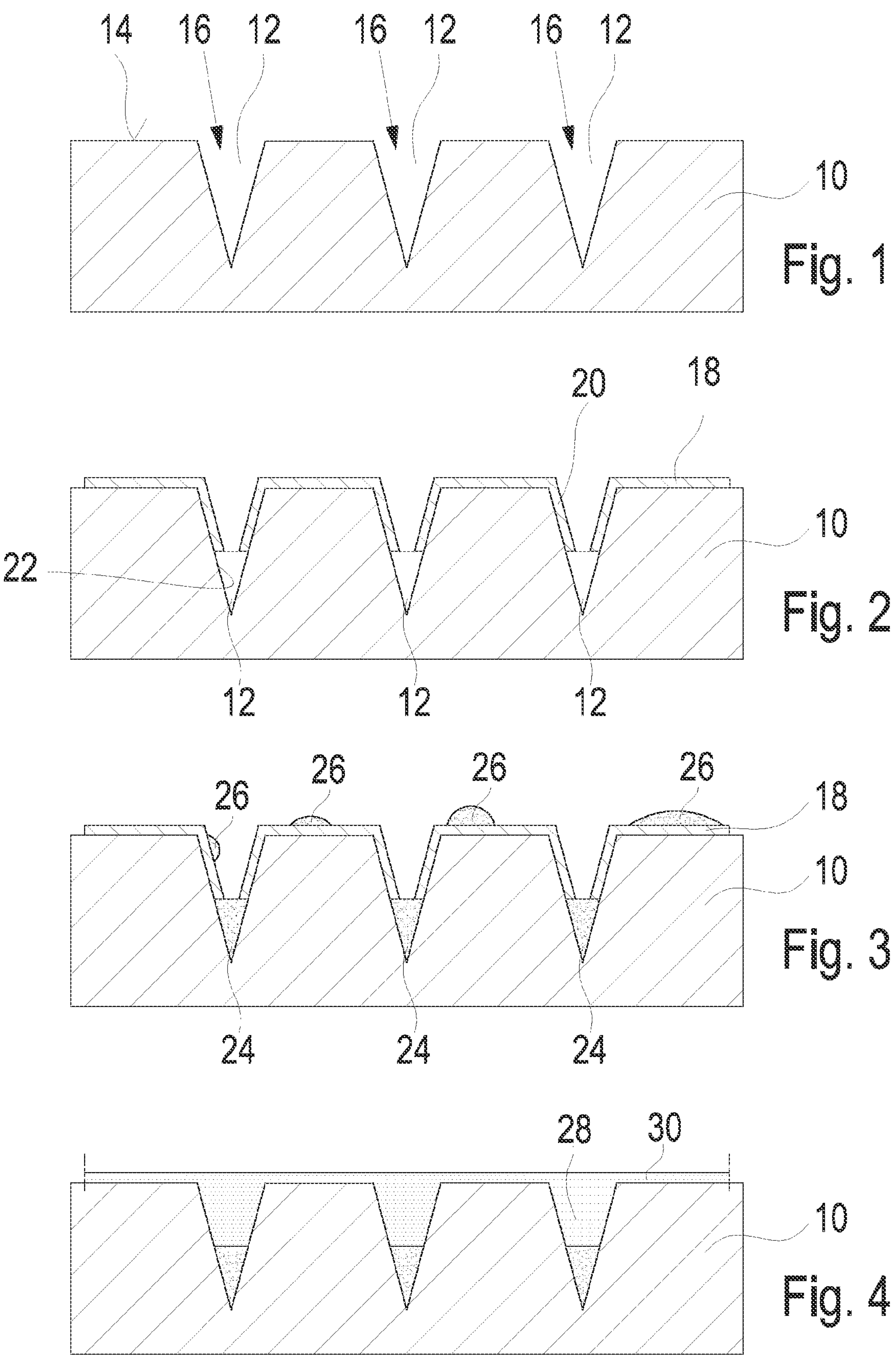
FIGS. 1 to 4 show an apparatus according to the disclosure for producing microarrays, in different states.

FIG. 1 is a schematic cross-section of a die 10 comprising a plurality of cavities 12. The cavities extend proceeding from an upper surface 14 of the die, such that the individual cavities 12 comprise openings 16 in the region of the upper surface.

Prior to metering an active agent-containing liquid, a cover element 18 (FIG. 2) is laid on the upper surface of the die 10. In this case, the cover element 18 is designed such that it covers the regions of the upper surface 14 which are formed between the cavities 12. The cover element 18 furthermore comprises projections 20. Said projections protrude into the cavities 12 and cover the inner walls 22 of the cavities in upper regions of the cavities, i.e. in regions facing in the direction of the upper surface 14 of the die 10.

Metering of the active agent-containing liquid takes place in the next step (FIG. 3). The corresponding liquid is arranged in the tips 24. Since metering exclusively into the cavities 12 is not possible, in particular on account of the small size of the cavities, some of the active agent-containing liquid is arranged on the cover element 18. These are drop-like regions 26 of the active agent-containing liquid.

Removing the cover element 18 also removes the active agent-containing liquid which is located on the cover element. A liquid, which does not contain any active agent, can then be metered in during a following step. Said liquid on the one hand fills the upper regions 28 of the cavities, and on the other hand forms a continuous cap layer 30. Following curing of the material, the microarray can be demolded from the die 10.

The invention claimed is:

1. A method for producing a microarray by means of an apparatus, the apparatus comprising:

a die comprising a plurality of microneedle cavities; and a cover element, wherein the cover element covers regions between the plurality of microneedle cavities during metering of an active agent-containing material into the plurality of microneedle cavities, wherein the cover element is removable after metering of the active agent-containing material such that there is no active agent-containing material in the regions covered by the cover element, and wherein the method comprises the steps of:

arranging the cover element on a die, such that regions between the plurality of microneedle cavities of the die are covered;

metering active agent-containing liquid into the plurality of microneedle cavities;

removing the cover element; and metering an active agent-free liquid into the plurality of microneedle cavities and onto an upper surface of the die for creating a support layer of the microarray.

2. The method for producing a microarray according to claim 1, in which a drying step is carried out prior to removing the cover element.

* * * * *